United States Patent
Wang et al.

(10) Patent No.: US 9,120,763 B2
(45) Date of Patent: Sep. 1, 2015

(54) METHOD FOR PRODUCING BENZOXAZINE COMPOUNDS

(75) Inventors: Dong Wang, The Woodlands, TX (US); Derek Scott Kincaid, Spring, TX (US)

(73) Assignee: Huntsman Advanced Materials Americas LLC, The Woodlands, TX (US)

( * ) Notice: Subject to any disclaimer, the term of this patent is extended or adjusted under 35 U.S.C. 154(b) by 0 days.

(21) Appl. No.: 14/232,656

(22) PCT Filed: Jul. 24, 2012

(86) PCT No.: PCT/US2012/047905
§ 371 (c)(1),
(2), (4) Date: Jan. 14, 2014

(87) PCT Pub. No.: WO2013/022595
PCT Pub. Date: Feb. 14, 2013

(65) Prior Publication Data
US 2014/0148597 A1     May 29, 2014

Related U.S. Application Data

(60) Provisional application No. 61/522,348, filed on Aug. 11, 2011.

(51) Int. Cl.
C07D 265/16     (2006.01)

(52) U.S. Cl.
CPC ................................. *C07D 265/16* (2013.01)

(58) Field of Classification Search
CPC ..................................................... C07D 265/16
USPC ............................................................ 544/90
See application file for complete search history.

(56) References Cited

U.S. PATENT DOCUMENTS

| | | |
|---|---|---|
| 2004/0068084 A1 | 4/2004 | Hwang et al. |
| 2010/0204385 A1 | 8/2010 | Kreiling et al. |
| 2010/0210810 A1 | 8/2010 | Katagiri et al. |

FOREIGN PATENT DOCUMENTS

| | | |
|---|---|---|
| JP | 2005 213301 | 8/2005 |
| WO | WO 03/011931 | 2/2003 |

*Primary Examiner* — Kahsay Habte

(57) ABSTRACT

The present disclosure provides a method for producing a benzoxazine compound by reacting a bi-functional phenol with formaldehyde and a mono-functional amine in the presence of a solvent system containing an apolar solvent and a polar aprotic solvent. Once formed, the benzoxazine compound may be precipitated from the reaction solution and dried to form a benzoxazine compound in powder form.

12 Claims, No Drawings

METHOD FOR PRODUCING BENZOXAZINE COMPOUNDS

CROSS-REFERENCE TO RELATED APPLICATION

Not applicable.

STATEMENT REGARDING FEDERALLY SPONSORED RESEARCH OR DEVELOPMENT

Not applicable.

FIELD OF INVENTION

This disclosure relates to a method for producing benzoxazine compounds from a phenolic compound, an aldehyde compound and an amine compound in the presence of a solvent system containing an apolar solvent and a polar aprotic solvent.

BACKGROUND OF THE INVENTION

Benzoxazine compounds can be synthesized by reacting a phenol with an amine and an aldehyde in the presence or absence of a solvent. The benzoxazine product is then isolated from the reaction solution by evaporation or precipitating the product from solution via a poor solvent.

In U.S. Pat. Publ. No. 2010/0210810, a process is disclosed for preparing high molecular weight benzoxazines which includes reacting a bifunctional phenol with a diamine and an aldehyde in a mixed solvent system containing an aromatic nonpolar solvent and an alcohol. Condensation water is then subsequently evaporated and the benzoxazine may be recovered from the reaction mixture by precipitation or spray-drying.

U.S. Pat. Publ. No. 2009/0270615 discloses a process whereby benzoxazines are produced from a phenol, primary amine and an aldehyde in the presence of an alkyl ester. The alkyl ester is then subsequently removed at moderately low temperatures.

In a process disclosed in U.S. Pat. No. 7,041,772, a phenol is reacted with a primary amine and aldehyde in an organic solvent selected from an alcohol, ketone, ethylene glycol and aromatic type solvent. Condensation water and organic solvent are then subsequently removed from the system under heat and reduced pressure to produce a benzoxazine.

U.S. Pat. Publ. No. 2009/0054614 teaches a process wherein a specific phenol is reacted with a specific aromatic diamine and an aldehyde optionally in the presence of an aromatic, halogenic or ether solvent to produce a dihydrobenzoxazine. Methanol is subsequently added to precipitate the dihydrobenzoxazine product from solution, and the precipitate is then dried to form the dihydrobenzoxazine product.

U.S. Pat. Publ. No. 2009/0187003 also discloses a process for making a dihydrobenzoxazine from an aromatic phenol, an aliphatic diamine and an aldehyde in the presence of an aromatic, halogenic or ether solvent. The benzoxazine is precipitated from solution using a poor solvent and then dried.

Finally, U.S. Pat. No. 5,543,516 teaches a solventless method for preparing benzoxazines from a phenol, a primary amine and aldehyde.

Known processes for producing benzoxazines are, however, not without their difficulties. For example, it usually takes a relatively longer time than desired to carry out the reaction and separate the benzoxazine from the solvent and condensation water. In addition, some of the solvents used in the synthesis are toxic while others are only removable at elevated temperature conditions causing premature degradation and/or polymerization of some benzoxazine compounds. Furthermore, when the condensation water and solvent are removed under significantly reduced pressure, the temperature of the reaction solution abruptly drops causing the viscosity of the solution to increase making further processing and use extremely difficult.

Notwithstanding the state of the technology, it would be desirable to provide alternative methods for producing benzoxazines whereby the benzoxazines are easily obtained as a powder solid with low residual solvent content and with substantially reduced or no gelation occurring during their production.

SUMMARY OF THE INVENTION

The present disclosure provides a method for producing a benzoxazine compound. In one embodiment, the benzoxazine compound is produced by the steps of
  (a) preparing a reaction solution containing (i) reactants comprising a phenolic compound, an amine compound and an aldehyde compound, and (ii) a solvent system including an apolar solvent and a polar aprotic solvent; and
  (b) exposing the reaction solution to reaction conditions at which the reactants combine chemically and maintaining the reactants at the reaction conditions to form the benzoxazine compound.

Once formed, the benzoxazine compound may be precipitated from the reaction solution and dried to form a benzoxazine compound in powder form that, in an embodiment, is substantially solvent-free.

In another embodiment, there is provided a method for producing a benzoxazine compound by the steps of:
  (a) preparing a reaction solution containing (i) reactants comprising a phenolic compound, an amine compound and an aldehyde compound, and (ii) a solvent system including an apolar solvent and optionally a polar aprotic solvent;
  (b) exposing the reaction solution to reaction conditions at which the reactants combine chemically and maintaining the reactants at the reaction conditions to form the benzoxazine compound;
  (c) optionally evaporating condensation water produced during reaction;
  (d) removing the apolar solvent from the reaction solution after completion of the reaction and contacting the reaction solution with a polar aprotic solvent; and
  (e) precipitating the benzoxazine compound from the reaction solution.

The benzoxazine compound may then be and dried to form a benzoxazine compound in powder form that, in an embodiment, is substantially solvent-free.

The benzoxazine compound produced according to the method of the present disclosure may be combined with other components to form a thermosetting resin composition which may be used in a variety of applications such as in coating, adhering, laminating and impregnating applications.

DETAILED DESCRIPTION OF THE INVENTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising"

may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical object of the article. By way of example, "a phenolic compound" means one phenolic compound or more than one phenolic compound. The phrases "in one embodiment," "according to one embodiment," and the like generally mean the particular feature, structure, or characteristic following the phrase is included in at least one embodiment of the present invention, and may be included in more than one embodiment of the present disclosure. Importantly, such phases do not necessarily refer to the same embodiment. If the specification states a component or feature "may", "can", "could", or "might" be included or have a characteristic, that particular component or feature is not required to be included or have the characteristic.

As used herein, "substantially solvent-free" is meant to say that minimal, preferably no solvent (i.e. solvent system plus poor solvent) or water is present in the benzoxazine compound except for trace amounts. Preferably any such amounts are less than 2% by weight, more preferably less than 1.0% by weight, even more preferably less than 0.5% by weight and especially less than 0.25% by weight relative to the total weight of the benzoxazine compound.

The term "apolar solvent" refers to a solvent which has a low dielectric constant ($\in$), preferably less than 9.5, and is not miscible with water The term "polar aprotic solvent" refers to a polar solvent which does not contain acidic hydrogen and does not act as a hydrogen bond donor In one embodiment, the present disclosure provides a method for producing a benzoxazine compound by reacting a phenolic compound with an amine compound and an aldehyde compound in a solvent system containing an apolar solvent and a polar aprotic solvent. The benzoxazine compound may subsequently be recovered from the reaction solution in powder form by evaporation and/or precipitation and/or drying. As used herein, the term "powder form" refers to a particulate that is solid and free flowing at ambient conditions. It has been surprisingly found that the method of the present disclosure not only eliminates gelation often seen during state of the art processing, but also provides for the production of various structural/molecular weight benzoxazine compounds, utilizes solvents which may be easily recycled, and can also produce a benzoxazine compound recovered in powder form that is substantially solvent-free.

In another embodiment, there is a provided a method for producing a benzoxazine compound by reacting a phenolic compound with an amine compound and an aldehyde compound in a solvent system containing an apolar solvent and optionally a polar aprotic solvent. The benzoxazine compound may then be subsequently recovered from the reaction solution in powder form by evaporation of the apolar solvent, preferably substantially all of the apolar solvent, after completion of the reaction, then addition of a polar aprotic solvent to the reaction solution prior to precipitation and/or drying. It has been surprisingly found that addition of the polar aprotic solvent to the reaction solution, after completion of the reaction and removal of the apolar solvent allows for improved efficiency in precipitation of the benzoxazine compound.

Thus, according to one embodiment, the method of the present disclosure includes step (a) preparing a reaction solution containing (i) reactants comprising a phenolic compound, an amine compound, an aldehyde compound, and (ii) a solvent system including an apolar solvent and a polar aprotic solvent.

In one embodiment, the phenolic compound is a mono-functional phenol. Examples of mono-functional phenols include, but are not limited to, phenol, o-cresol, p-cresol, m-cresol, p-tert-butylphenol, p-octylphenol, p-cumylphenol, dodecylphenol, o-phenylphenol, p-phenylphenol, 1-naphthol, 2-naphthol, m-methoxyphenol, p-methoxyphenol, m-ethoxyphenol, dimethylphenol, 3,5-dimethylphenol, xylenol, 2-bromo-4-methylphenol and 2-allylphenol.

In another embodiment, the phenolic compound is a bi-functional phenol. Examples of bi-functional phenols include, but are not limited to, compounds having a formula (1), (2) or (3):

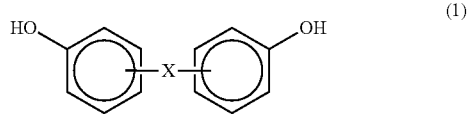

(1)

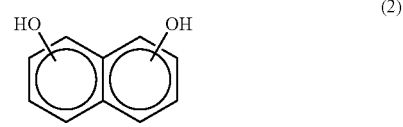

(2)

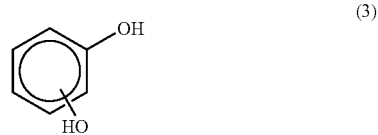

(3)

where X is a direct bond, an aliphatic group, an alicyclic group or an aromatic group which may contain a hetero element or functional group. In formula (2), X may be bonded to an ortho position, meta position or para position of each hydroxyl group.

In one embodiment, X has one of the following structures:

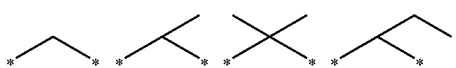

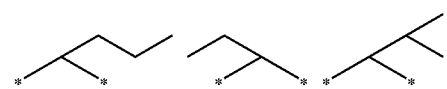

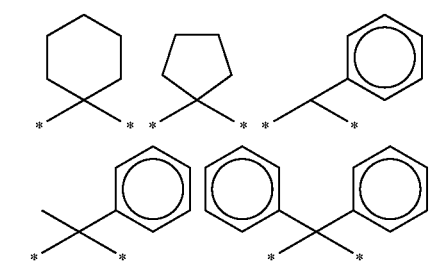

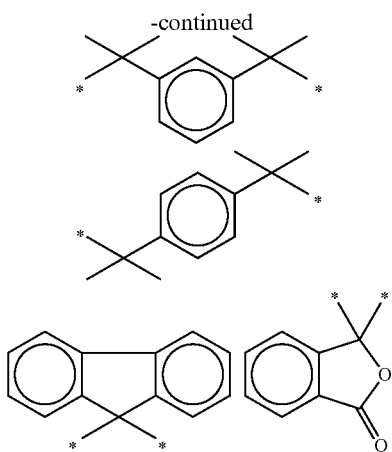

where * represents a binding site to a benzene ring in formula (2).

In yet another embodiment, the phenolic compound is a poly-functional phenol, such as, a trisphenol compound, for example, 1,3,5-trihydroxy benzene, a phenol-novolac resin, a styrene-phenol copolymer, a xylene-modified phenol resin, a melamine-modified phenol resin, a xylylene-modified phenol resin or a biphenylene-modified phenol resin.

In the present disclosure the phenolic compounds may be used independently or in combination of two or more.

According to another embodiment, the amine compound is a monofunctional amine. Examples of monofunctional amines include, but are not limited to, ammonium, methylamine, ethylamine, propylamine, butylamine, isopropylamine, hexylamine, octadecylamine, cyclohexylamine, 1-aminoanthracene, 4-aminobenzaldehyde, 4-aminobenzophenone, aminobiphenyl, 2-amino-5-bromo pyridine, D-3-amino-∈-caprolactam, 2-amino-2,6-dimethylpiperidine, 3-amino-9-ethylcarbozole, 4-(2-aminoethyl)morpholine, 2-aminofluorene, 1-aminohomopiperidine, 9-aminophenanthrene, 1-aminopyrene, 4-bromoaniline, aniline and mixtures thereof.

In another embodiment, the amine compound is a difunctional amine. Examples of difunctional amines include, but are not limited to, aromatic diamines such as o-phenylene diamine, m-phenylene diamine, p-phenylene diamine, benzidine, furfurylamine, 1,4-diaminobenzene, 2-aminobenzylamine, 4,4'-methylenedianiline, 4,4'-methylenedi-o-toludine, 4,4'-diaminodiphenylether, 2,2'-bis[4-(4-aminophenoxy)phenyl]propane, 4,4'-[1,3-phenylenebis(1-methyl-ethylidene)]bisaniline, 4,4'-[1,4-phenylenebis(1-methyl-ethylidene)]bisaniline, 1,3-bis(4-aminophenoxy) benzene, 1,4-bis(4-aminophenoxy)benzene, 2,7-diaminofluorene, 9,10-diaminophenanthranene, 1,4-diaminobenzophenone, 4,4'-diaminodiphenylsulfone, 4,4'-diaminophenylsulfide, and 4,4'-oxydianiline; alicyclic diamines such as 1,4-diaminocyclohexane, 1,4-diaminopiperazine, 3(4),8(9)-bis(aminomethyl)tricycle[5,2,1,0$^{2,6}$]decane, 2,5(6)-bis(aminomethyl)bicycle[2.2.1]heptane; and aliphatic diamines such as 1,2-diaminoethane, 1,3-diaminopropane, 1,4-diaminobutane, 1,6-diaminohexane, 1,10-diaminodecane, 1,12-diaminododecane, 1,14-diaminotetradecane and 1,18-diaminooctadecane.

In still another embodiment, the amine compound is a tri-functional amine. Examples of tri-functional amines include, but are not limited to, melamine and tris(2-aminoethyl)amine.

In still yet another embodiment, the amine compound is a tetra-functional amine. Examples of tetra-functional amines include, but are not limited to, fluorenetetraamine and tetraamine-diphenylether.

In a further embodiment, the amine compound is an amine-functionalized polydimethylsiloxane or a copolymer thereof; an amine-functionalized polybutadiene or a copolymer thereof; or polyallylamine.

In the present disclosure, the amine compounds may be used independently or in combination of two or more.

According to another embodiment, the aldehyde compound may be any aldehyde, such as, but not limited to, formaldehyde, acetaldehyde, propionaldehyde or butylaldehyde, or an aldehyde derivative such as, but not limited to, paraformaldehyde and polyoxymethylene, with formaldehyde and paraformaldehyde being preferred. The aldehyde compound may also be a mixture of aldehydes and/or aldehyde derivatives.

In one preferred embodiment, the aldehyde compound is a compound having the formula QCHO, where Q is hydrogen, an aliphatic group having from 1 to 6 carbon atoms, or a cyclic group having 1 to 12 carbon atoms, with 1 to 6 carbon atoms being preferred. Preferably Q is hydrogen.

According to an embodiment, the solvent system includes an apolar solvent and a polar aprotic solvent. In another embodiment, the solvent system consists essentially of the apolar solvent and the polar aprotic solvent. In still another embodiment, the solvent system contains the apolar solvent and optionally the polar aprotic solvent.

Examples of apolar solvents include, but are not limited to, those selected from pure benzene, mixed benzene, toluene, xylene, ethylbenzene, octane, methylcyclohexane, butylbenzene, cumene, mesitylene, chlorobenzene, dichlorobenzene, o-chlorotoluene, n-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, tetrachloroethylene and mixtures thereof. In one preferred embodiment, the apolar solvent is toluene, xylene or a mixture thereof.

Examples of polar aprotic solvents include, but are not limited to, those selected from dimethyl sulfoxide, N,N-dimethylformamide, N,N-dimethylacetamide, hexamethylphosphoramide, N-methyl-2-pyrrolidone, acetone, acetonitrile, 1,4-dioxane, tetrahydrofuran and mixtures thereof.

The proportion of apolar solvent and polar aprotic solvent in the solvent system may vary. Thus, in one embodiment, the solvent system may contain about 5% by volume to about 50% by volume of the polar aprotic solvent, based on the total volume of the solvent system. In another embodiment, the solvent system may contain about 50% by volume to about 95% by volume of the apolar solvent, based on the total volume of the solvent system. In still another embodiment, the solvent system may contain from about 5% by volume to about 50% by volume of the polar aprotic solvent, based on the total volume of the solvent system, and from about 50% by volume to about 95% by volume of the apolar solvent, based on the total volume of the solvent system. In still a further embodiment, the solvent system contains at least about 99% by volume of the apolar solvent and polar aprotic solvent, based on the total volume of the solvent system.

When preparing the reaction solution, the phenolic compound, aldehyde compound, amine compound and solvent system may be contacted or mixed in any particular order. Because the reaction is exothermic, attention should be paid to an abrupt temperature increase of the reaction solution once the reactants have been combined. According to one embodiment, the phenolic compound is first dissolved into the solvent system. The aldehyde compound is then subsequently added to the system, and the system mixed thoroughly. The amine compound is then added, in portions or continuously, to form the reaction solution.

The amounts of phenolic compound, aldehyde compound and amine compound used in preparing the reaction solution may vary and will depend on their chemical nature, e.g. the number of reactive groups taking part in the reaction. The stoichiometry is well within the skill of those conversant in the art, and the required relative amounts of reactants are readily selected depending on the functionality of the reactants. However, in one particular embodiment, about 0.5 mol to about 1.2 mol of the amine compound per mol of the phenolic compound is used. In another embodiment, about 0.75 mol to 1.1 mol of the amine compound per mol of the phenolic compound is used. In yet another embodiment, about 1.7 mol to about 2.3 mol of the aldehyde compound per mol of the amine compound is used. In still another embodiment, about 1.8 mol to 2.2 mol of the aldehyde compound per mol of the amine compound is used. In another embodiment, the molar ratio of phenolic compound to aldehyde compound may be from about 1:3 to 1:10, preferably from about 1:4: to 1:7, and more preferably from about 1:4.5 to 1:5 and the molar ratio of phenolic compound to amine compound may be from about 1:1 to 1:3, preferably from about 1:1.4 to 1:2.5, and more preferably from about 1:2.1 to 1:2.2.

While no catalyst is required for use in the reaction leading to the benzoxazine compound, in one embodiment, an acid catalyst or basic catalyst may be employed and added to the reaction solution. Examples of suitable acid catalysts include, but are not limited to, those selected from HCl, trifluoroacetic acid, methane sulfonic acid, p-toluenesulfonic acid, trifluoromethanesulfonic acid, benzoic acid and mixtures thereof. Examples of basic catalysts include, but are not limited to, those selected from NaOH, $Na_2CO_3$, triethylamine, triethanolamine and mixtures thereof. The acid catalyst or basic catalyst may be added during or after formation of the reaction solution.

According to another embodiment, the method of the present disclosure includes step (b) exposing the reaction solution to a reaction condition at which the reactants combine chemically and maintaining the reactants at the reaction condition to form the benzoxazine compound.

With respect to the reaction conditions, the reaction may proceed at about room temperature given sufficient time, or may be conducted under heat at a controlled temperature of between about 40° C. to about 150° C. The pressure during the reaction may be atmospheric pressure or a pressure of up to about 100 psi. The time of reaction will depend on the nature of the reactants as well as the reaction conditions. In one embodiment, the reaction is allowed to proceed for at least about 15 minutes, preferably at least about 30 minutes, more preferably at least about 1 hour, and even more preferably at least about 2 hours. In another embodiment, the reaction is allowed to proceed for a period of time of between about 15 minutes and 10 hours. After reaction is complete, the reaction solution may be removed from heat and allowed to cool or it may be cooled using a refrigerant.

According to another embodiment, the method of the present disclosure may include further step (c) evaporating condensation water produced during reaction. This step (c), whereby condensation water is evaporated from the reaction solution, is not particularly limited and may be performed by azeotropically evaporating the condensation water with the solvent system in the reaction solution. The condensation water may be evaporated by, for example, use of an isobaric dropping funnel with a cock, a Dimroth condenser, a Dean-Stark device or the like.

In another embodiment, the method of the present disclosure may include a further step (d) removing the apolar solvent from the reaction solution after completion of the reaction. Whether this step is employed or not will depend on the chemical nature of the reactants, the reaction conditions, and/ or which poor solvent may be utilized to precipitate the benzoxazine compound from the reaction solution. For example, when water is utilized as a poor solvent, it's desirable to remove substantially all apolar solvent from the reaction solution before precipitation is initiated due to the incompatibility of water and apolar solvent. In addition, it is desirable to remove substantially all of apolar solvent when lower molecular weight benzoxazine compounds are produced so that more efficient precipitation and further processing can be achieved. According to an embodiment, the amount of the apolar solvent removed in step (d) may be at least about 1% by volume of the apolar solvent, based on the total volume of the reaction solution, preferably at least about 25% by volume of the apolar solvent, based on the total volume of the reaction solution, more preferably at least about 50% by volume of the apolar solvent, based on the total volume of the reaction solution, even more preferably at least about 75% by volume of the apolar solvent, based on the total volume of the reaction solution, and even more preferably at least about 99% by volume of the apolar solvent, based on the total volume of the reaction solution. During and/or after removal of the apolar solvent, additional polar aprotic solvent may optionally be added to the reaction solution to control viscosity. Thus, in one particular embodiment, substantially all of the apolar solvent is removed from the reaction solution after completion of the reaction and polar aprotic solvent is added to the reaction solution. In one embodiment, the amount of polar aprotic solvent added to the reaction solution may range from about 0.5% by volume to about 90% by volume of polar aprotic solvent, based on the total volume of the reaction solution.

According to still another embodiment, the method of the present disclosure may include a further step (e) precipitating the benzoxazine compound from the reaction solution by contacting the reaction solution with a poor solvent. The poor solvent utilized in this step may include, but is not limited to, water or an alcohol, for example, a low boiling temperature alcohol such as methanol. The temperature during precipitation will depend on the benzoxazine compound as well as the poor solvent utilized, and therefore in one embodiment, may range from about 0° C. to about 70° C.

In yet another embodiment, the method of the present disclosure may include a further step (f) drying the precipitated benzoxazine compound to form a benzoxazine compound in powder form that is substantially solvent-free. The precipitated benzoxazine may be dried by any conventional means, such as, for example by air drying at ambient conditions or by drying under the application of heat, such as by oven drying.

According to one particular embodiment, the method of the present disclosure produces a benzoxazine compound which may be represented by the general formula

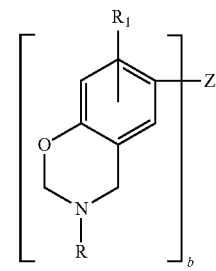

wherein b is an integer from 1 to 4; R is a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; $R_1$ is hydrogen, an alkyl group, an alkenyl group or an aryl group; and Z is a direct bond (when b=2), a substituted or unsubstituted $C_1$-$C_{20}$ alkylene group, a substituted or unsubstituted $C_6$-$C_{20}$ arylene group, a substituted or unsubstituted $C_2$-$C_{20}$ heteroarylene group, S, S=O, O=S=O or C=O.

The benzoxazine compound produced in the method of the present disclosure may be combined with one or more optional components, such as an epoxy resin, a polyphenylene ether resin, a polyimide resin, a silicone resin, a melamine resin, an urea resin, an allyl resin, a polyester resin, a bismaleimide resin, an alkyd resin, a furan resin, a polyurethane resin, an aniline resin, a curing agent, a flame retardant, a filler, a release agent, an adhesion-imparting agent, a surfactant, a colorant, a coupling agent, and/or a leveling agent to form a thermosetting resin which can then be subsequently used in a variety of applications, such as, casting, laminating, impregnating, coating, adhering, sealing, painting, binding, insulating, or in embedding, pressing, injection molding, extruding, sand mold binding, foam and ablative materials.

EXAMPLES

Example 1

Into a four-neck flask equipped with a mechanical stirrer, a Dean-Stark trap and a reflux condenser, were charged 95 g of phenolphthalein, 43 g of paraformaldehyde, 100 g toluene and 10 g of dimethylacetamide. The flask containing the reaction solution was then heated to about 85° C., then 56 g of aniline was gradually added to the reaction solution and the reaction was allowed to proceed for several hours. The temperature was then gradually increased to about 116° C. to remove condensation water azeotropically. After allowing for a six hour post-reaction time period, toluene was removed by vacuum at a temperature of about 80° C. Approximately 190 g of dimethylacetamide was then further added to dilute the reaction solution. After allowing the reaction to cool to room temperature, about 1% by weight of triethylamine, based on the total weight of the reaction solution, was added to the reaction solution. The benzoxazine compound was then precipitated by contacting it with water. The white precipitate was then washed with water and dried in a vacuum oven at a temperature of about 60° C. for 24 hours. The benzoxazine compound in powder form exhibited a residual content of 0.29% by weight dimethylacetamide, 0.05% by weight toluene and 0.3% by weight of water, based on the total weight of the benzoxazine compound in powder form.

Example 2

Into a four-neck flask equipped with a mechanical stirrer, a Dean-Stark trap and a reflux condenser, were charged 436 g of phenolphthalein, 218 g of paraformaldehyde, 500 g toluene and 50 g of dimethylacetamide. The flask containing the reaction solution was heated to about 85° C., then 280 g of aniline was gradually added to the reaction solution and the reaction was allowed to proceed for several hours. The temperature was then gradually increased to about 116° C. to remove condensation water azeotropically. After allowing for a six hour post-reaction time period, toluene was removed by vacuum at a temperature of about 80° C. Approximately 858 g of dimethylacetamide was then further added to dilute the reaction solution and the reaction solution was allowed to cool to room temperature. The benzoxazine compound was then precipitated by contacting the reaction solution with methanol. The white precipitate was then washed with methanol and dried under a hood. The benzoxazine compound in powder form exhibited a residual content of 0.4% by weight dimethylacetamide and 0% by weight toluene, based on the total weight of the benzoxazine compound in powder form.

Example 3

Into a four-neck flask equipped with a mechanical stirrer, a Dean-Stark trap and a reflux condenser, were charged 91 g of bisphenol A, 51 g of paraformaldehyde, 400 g toluene and 40 g of dimethylacetamide. The flask containing the reaction solution was then heated to about 60° C., then 54 g of m-xylenediamine was gradually added to the reaction solution and the reaction was allowed to proceed for several hours. The temperature was then gradually increased to about 110° C. to remove condensation water azeotropically. The benzoxazine compound was then precipitated by contacting the reaction solution with methanol. The white precipitate was then washed with methanol and dried at room temperature.

Example 4

Into a four-neck flask equipped with a mechanical stirrer, a Dean-Stark trap and a reflux condenser, were charged 18 g of bisphenol A, 21 g of paraformaldehyde, 142 g toluene and 40 g of dimethylacetamide. The flask containing the reaction solution was then heated to about 80° C., then 18 g of 1,2-diaminocyclohexane was gradually added to the reaction solution and the reaction was allowed to proceed for several hours. The temperature was then gradually increased to about 100° C. to remove condensation water azeotropically, during which about 200 g of additional toluene was added to lower the reaction solution's viscosity. After the reaction solution was allowed to cool to room temperature, the benzoxazine compound was precipitated by contacting the reaction solution with methanol. The white precipitate was then washed with methanol and dried at room temperature.

Example 5

Into a four-neck flask equipped with a mechanical stirrer, a Dean-Stark trap and a reflux condenser, were charged 36 g of bisphenol A, 21 g of paraformaldehyde, 144 g toluene and 32 g of dimethylacetamide. The flask containing the reaction solution was then heated to about 85° C., then 28 g of diethyl toluene diamine was gradually added to the reaction solution and the reaction was allowed to proceed for seven hours. The temperature was then gradually increased to about 110° C. to remove condensation water azeotropically. After the reaction solution was allowed to cool to room temperature, the benzoxazine compound was precipitated by contacting the reaction solution with methanol. The white precipitate was then washed with methanol and dried at room temperature.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A method for producing a benzoxazine compound comprising the steps of:
   (a) preparing a reaction solution containing (i) reactants including a bi-functional phenol, a mono-functional amine and formaldehyde and (ii) a solvent system including an apolar solvent selected from pure benzene, mixed benzene, toluene, xylene, ethylbenzene, octane, methylcyclohexane, butylbenzene, cumene, mesitylene, chlorobenzene, dichlorobenzene, o-chlorotoluene, n-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, tetrachloroethylene and a mixture thereof and a polar aprotic solvent selected from dimethyl sulfoxide, N,N-dimethylformamide, N,N-dimethylacetamide, hexamethylphosphoramide, N-methyl-2-pyrrolidone, acetone, acetonitrile, 1,4-dioxane, tetrahydrofuran and a mixture thereof; and
   (b) exposing the reaction solution to reaction conditions at which the reactants combine chemically and maintaining the reaction solution at the reaction condition to form the benzoxazine compound wherein the benzoxazine compound is a compound of the formula

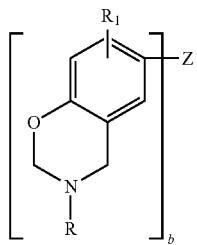

wherein b is an integer from 1 to 4; R is a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; $R_1$ is hydrogen, an alkyl group, an alkenyl group or an aryl group; and Z is a direct bond (when b=2), a substituted or unsubstituted $C_1$-$C_{20}$ alkylene group, a substituted or unsubstituted $C_6$-$C_{20}$ arylene group, a substituted or unsubstituted $C_2$-$C_{20}$ heteroarylene group, S, S=O, O=S=O or C=O.

2. The method of claim 1 wherein the hi-functional phenol is a compound having a formula (1), (2) or (3):

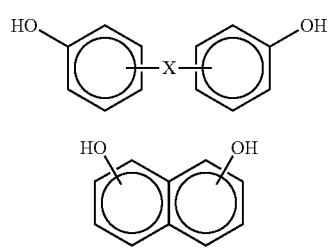

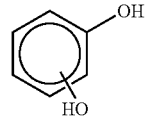

where X is a direct bond, an aliphatic group, an alicyclic group or an aromatic group which may contain a hetero element or functional group.

3. The method of claim 1 wherein the solvent system contains from about 5% by volume to about 50% by volume of the polar aprotic solvent, based on the total volume of the solvent system.

4. The method of claim 3 wherein the solvent system contains from about 50% by volume to about 95% by volume of the apolar solvent, based on the total volume of the solvent system.

5. The method of claim 1 wherein the molar ratio of mono-functional amine to bi-functional phenol is about 0.5 mol to about 1.2 mol of the mono-functional amine per mol of the bi-functional phenol and the molar ratio of formaldehyde to mono-functional amine is about 1.8 mol to 2.2 mol of the formaldehyde compound per mol of the mono-functional amine.

6. The method of claim 1 wherein the reaction solution is exposed to a temperature of between about 40° C. and about 150° C. and a pressure of between atmospheric pressure up to about 100 psi.

7. The method of claim 1 further including the step (c) evaporating condensation water produced during reaction.

8. The method of claim 7 further including the steps (d) removing the apolar solvent from the reaction solution after completion of the reaction; and (e) precipitating the benzoxazine compound from the reaction solution by contacting the reaction solution with a poor solvent.

9. The method of claim 8 wherein the poor solvent is selected from water and methanol.

10. A method for producing a benzoxazine compound comprising the steps of:
    (a) preparing a reaction solution containing (i) reactants including a bi-functional phenol, a mono-functional amine and formaldehyde, and (ii) a solvent system including an apolar solvent selected from pure benzene, mixed benzene, toluene, xylene, ethylbenzene, octane, methyl cyclohexane, butylbenzene, cumene, mesitylene, chlorobenzene, dichlorobenzene, o-chlorotoluene, n-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, tetrachloroethylene and a mixture thereof and a polar aprotic solvent selected from dimethyl sulfoxide, N,N-dimethylformamide, N,N-dimethylacetamide, hexamethylphosphoramide, N-methyl-2-pyrrolidone, acetone, acetonitrile, 1,4-dioxane, tetrahydrofuran and a mixture thereof;
    (b) exposing the reaction solution to reaction conditions at which the reactants combine chemically and maintaining the reaction solution at the reaction condition to form the benzoxazine compound;
    (c) optionally evaporating condensation water produced during reaction;
    (d) optionally removing the apolar solvent from the reaction solution after completion of the reaction and optionally adding polar aprotic solvent to the reaction solution during and/of after removal of the apolar solvent;

(e) precipitating the benzoxazine compound from the reaction solution by contacting the reaction solution with a poor solvent; and (f) drying the precipitated benzoxazine compound wherein the benzoxazine compound is in powder form and is substantially solvent-free and is a compound of the formula

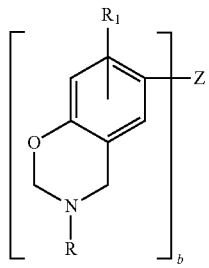

wherein b is an integer from 1 to 4; R is a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; $R_1$ is hydrogen, an alkyl group, an alkenyl group or an aryl group; and Z is a direct bond (when b=2), a substituted or unsubstituted $C_1$-$C_{20}$ alkylene group, a substituted or unsubstituted $C_6$-$C_{20}$ arylene group, a substituted or unsubstituted $C_2$-$C_{20}$ heteroarylene group, S, S=O, O=S=O or C=O.

11. The method of claim 10 wherein the benzoxazine compound contains less than 2% by weight (the solvent system plus the poor solvent plus water) relative to the total weight of the benzoxazine compound.

12. A method for producing a benzoxazine compound comprising the steps of:

(a) preparing a reaction solution containing (i) reactants including a bi-functional phenol, a mono-functional amine and formaldehyde compound, and (ii) a solvent system including an apolar solvent selected from pure benzene, mixed benzene, toluene, xylene, ethylbenzene, octane, methylcyclohexane, butylbenzene, cumene, mesitylene, chlorobenzene, dichlorobenzene, o-chlorotoluene, n-chlorotoluene, p-chlorotoluene, 1,2-dichloroethane, 1,2-dichloropropane, carbon tetrachloride, 1,1,1-trichloroethane, 1,1,2-trichloroethane, 1,1,1,2-tetrachloroethane, 1,1,2,2-tetrachloroethane, trichloroethylene, tetrachloroethylene and a mixture thereof and optionally a polar aprotic solvent selected from dimethyl sulfoxide, N,N-dimethylformamide, N,N-dimethylacetamide, hexamethylphosphoramide, N-methyl-2-pyrrolidone, acetone, acetonitrile, 1,4-dioxane, tetrahydrofuran and a mixture thereof;

(b) exposing the reaction solution to reaction conditions at which the reactants combine chemically and maintaining the reaction solution at the reaction condition to form the benzoxazine compound;

(c) optionally evaporating condensation water produced during reaction;

(d) removing the apolar solvent from the reaction solution after completion of the reaction and contacting the reaction solution with polar aprotic solvent selected from dimethyl sulfoxide, N,N-dimethylformamide, N,N-dimethylacetamide, hexamethylphosphoramide, N-methyl-2-pyrrolidone, acetone, acetonitrile, 1,4-dioxane, tetrahydrofuran and a mixture thereof during and/or after removal;

(e) precipitating the benzoxazine compound from the reaction solution by contacting the reaction solution with a poor solvent; and (f) drying the precipitated benzoxazine compound wherein the benzoxazine compound is in powder form and is substantially solvent-free and is a compound of the formula

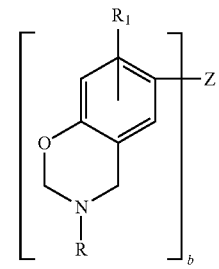

wherein b is an integer from 1 to 4; R is a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; $R_1$ is hydrogen, an alkyl group, an alkenyl group or an aryl group; and Z is a direct bond (when b=2), a substituted or unsubstituted $C_1$-$C_{20}$ alkylene group, a substituted or unsubstituted $C_6$-$C_{20}$ arylene group, a substituted or unsubstituted $C_2$-$C_{20}$ heteroarylene group, S, S=O, O=S=O or C=O.

* * * * *